United States Patent
Lessard et al.

(10) Patent No.: US 6,708,122 B2
(45) Date of Patent: Mar. 16, 2004

(54) APPARATUS AND METHOD FOR DETECTING TWIST IN ARTICLES

(75) Inventors: Jean-Luc Lessard, Saint-Étienne de Lauzon (CA); Yvon Legros, Sainte-Foy (CA); Jean-Pierre Mongeau, Terrebonne (CA)

(73) Assignee: Centre de recherche industrielle du Québec, Montréal (CA)

( * ) Notice: Subject to any disclaimer, the term of this patent is extended or adjusted under 35 U.S.C. 154(b) by 0 days.

(21) Appl. No.: 10/310,815

(22) Filed: Dec. 6, 2002

(65) Prior Publication Data

US 2003/0109991 A1 Jun. 12, 2003

(51) Int. Cl.⁷ .............................................. G06F 19/00
(52) U.S. Cl. ...................................................... 702/42
(58) Field of Search .............................. 702/33, 35, 40, 702/42, 105, 150, 151, 152, 153; 250/306, 307, 492.1

(56) References Cited

U.S. PATENT DOCUMENTS 4,460,160 A     7/1984  Tillotson
4,774,988 A    10/1988  Washburn et al.
6,122,065 A *   9/2000  Gauthier ..................... 356/394
6,293,152 B1    9/2001  Stanish et al.

FOREIGN PATENT DOCUMENTS

CA            2297879     *  8/2001

* cited by examiner

Primary Examiner—Michael Nghiem
(74) Attorney, Agent, or Firm—Jean-Claude Boudreau

(57) ABSTRACT

An apparatus and method for detecting twist in an articles such as pieces of lumber being carried on a high-speed longitudinally moving conveyer use a non-contact scanning technique according to which a pair of transverse scan line beams is directed onto a surface of the article in spaced relationship in the conveying direction, and successive scans of corresponding simultaneously scanned pairs of spaced transverse areas on the article are repeatedly performed while the article is conveyed, to generate profile data characterizing position of each transverse area in a reference system. The profile data characterizing the respective position of both transverse areas is compared with one another to generate partial twist indicative data associated with each scan, followed by a summation of the partial twist indicative data associated with all scans to obtain an indication of the twist in the considered portion of the article.

33 Claims, 7 Drawing Sheets

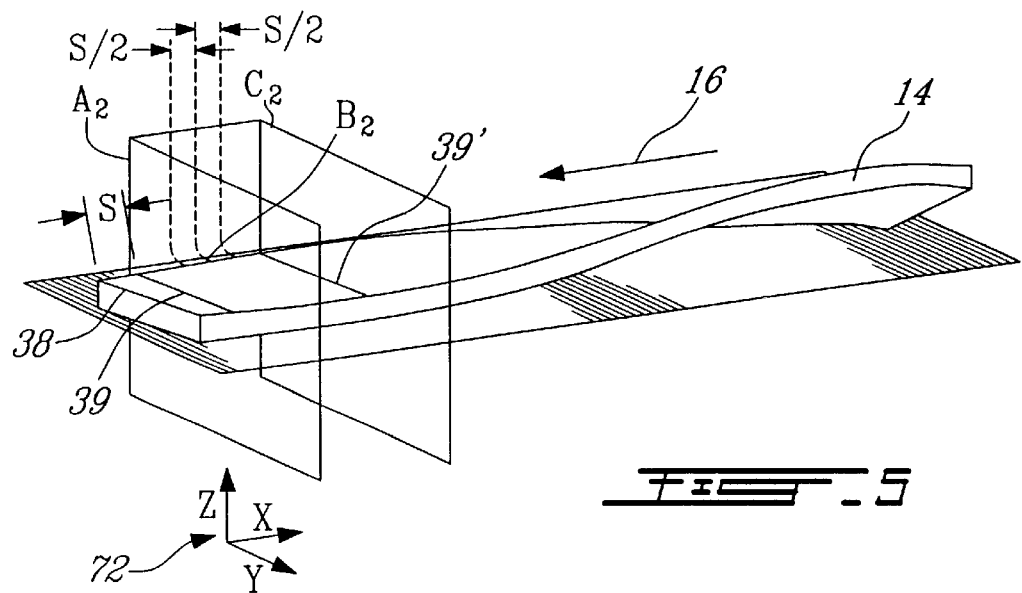
FIG. 5
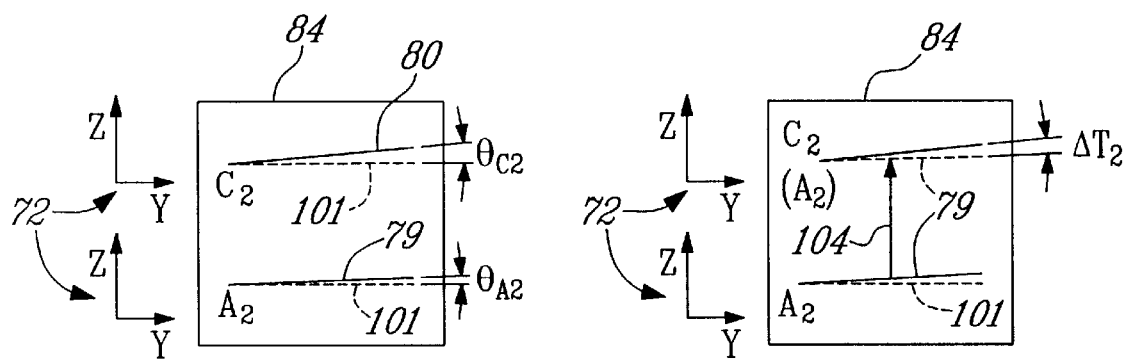
FIG. 5a
FIG. 5b

APPARATUS AND METHOD FOR DETECTING TWIST IN ARTICLES

FIELD OF THE INVENTION

The present invention relates to the field of non-contact scanning techniques for detecting geometrical defects in articles, and more particularly to non-contact apparatus and method for detecting twist in articles such as pieces of lumber.

BRIEF DESCRIPTION OF THE PRIOR ART

Non-contact systems for detecting geometrical and surface defects in articles, such as for detecting wane, holes, knots and roughness in pieces of lumber/timber and for generating grading and/or optimizing information based on such defects detection are known. An example of such a system is disclosed in U.S. Pat. No. 6,122,065 issued on Sep. 19, 2000 to Labbe et al. to the name of the present assignee, which system detects surface defects on a piece of lumber freely carried on a conveyer, in presence of some relative movement occurring between the piece of lumber and the conveyer surface while the inspection is performed. The system includes an inspection unit integrating an optical ranging subsystem using a laser and a camera for obtaining profile data through triangulation-based derivation techniques. Although the system of Labbe et al. is particularly efficient to detect roughness, cavities, wane, missing wood and altered wood on pieces of lumber that are conveyed at high speed, lumber grading based on the detection of these defects generally require the consideration of other deformation-related defects such as bow, cup, crook and twist.

Bow, cup and crook are all associated with two-dimensional edge profile deformations within planes that are respectively perpendicular/longitudinal, perpendicular/transverse and parallel/longitudinal to a main surface of the piece of lumber. Although the assessment of bow, cup and crook generally still involves human-based inspection in many mills, the two-dimensional deformation characteristics shared by bow, cup and crook are advantageously used for their measurements in a known automated method disclosed in U.S. Pat. No. 4,774,988 issued on Oct. 4, 1988 to Washburn et al., which method consists of applying successive, overlapping scans involving three (3) simultaneous measurements of edge distance with respect to a baseline while the piece of lumber is transported, determining for each scan any deviation from linearity of an interior position corresponding to a central one of the three (3) measurements, and computing an edge profile of the piece of lumber based on all deviations. Although being applicable to bow, cup or crook measurements, such method cannot be applied to the measurement of twist since it does not involve any edge profile.

In Canadian Patent Application no. 2,297,879 published on Aug. 3, 2001 to Carpentier, a non-contact method and apparatus for determining the shape of a workpiece in movement on a conveyor is disclosed, which uses a profiling unit including two or more laser diodes and a camera for capturing sets of profile images of the piece at predetermined intervals of time, wherein the last profile images of a given set are juxtaposed to the first profile images of a next set in an overlapping relationship, which profile images of overlapping sets as taken at different times are then correlated and transformed by an analyzing computer to compensate for wobbling movement of the workpiece that would otherwise skew the shape data. Although Carpentier teaches that such apparatus and method can be used to measure twist as well as bow and crook from the shape data obtained, the position of the overlapping images must be accurately measured and/or controlled to ensure that the transformation as operated by the analyzing computer does not generate cumulative error data components which may become significant in cases where the shape data is obtained over a large workpiece portion. It is difficult in practice to warrant that a shape inspecting system for use in combination with a high-speed workpiece conveyor be always calibrated in such a manner to maintain shape measurement errors within acceptable limits. Therefore, there is still a need for accurate, non-contact automated apparatus and method for measuring twist in articles such as pieces of lumber.

SUMMARY OF THE INVENTION

It is therefore a main object of the present invention to provide an apparatus and method for measuring twist in an article while being transported on a conveyor, which are substantially insensitive to relative movement between the article and the conveying surface, without suffering from accuracy limitations experienced with known prior art systems.

According to the above main object, from a broad aspect of the present invention, there is provided an apparatus for detecting twist along a reference axis in at least a portion of an article being carried on a conveyer in a conveying direction substantially parallel to the reference axis, the apparatus comprising a surface profile sensing unit mounted with respect to the conveyor and provided with a non-contact scanning device directing a pair of transverse scan line beams onto a surface of the article in spaced relationship in the conveying direction and repeatedly performing scans of corresponding simultaneously scanned pairs of spaced transverse areas of said surface while the article is conveyed, to generate profile data characterizing position of each transverse area in a reference system. The apparatus further comprises a data processor device for comparing with one another the profile data characterizing the respective position of the transverse areas of each scan to generate partial twist indicative data associated with each scan, and for summing the partial twist indicative data associated with all scans to obtain an indication of the twist in the article portion.

According to another broad aspect of the invention, there is provided a method for detecting twist along a reference axis in at least a portion of an article being carried on a conveyer in a conveying direction substantially parallel to the reference axis, the method comprising the steps of: i) directing a pair of transverse scan line beams onto a surface of the article in spaced relationship in the conveying direction while repeatedly performing scans of corresponding simultaneously scanned pairs of spaced transverse areas of said surface while the article is conveyed, to generate profile data characterizing position of each said transverse area in a reference system; ii) comparing with one another the profile data characterizing the respective position of the transverse areas of each scan to generate partial twist indicative data associated with each scan; and iii) summing the partial twist indicative data associated with all scans to obtain an indication of the twist in the article portion.

BRIEF DESCRIPTION OF THE DRAWINGS

Preferred embodiments of an apparatus and method according to the present invention will now be described in detail in view of the accompanying drawings in which:

FIG. 5 is a schematic view of the piece of lumber at a second scanning position showing a second pair of transverse areas of the piece of piece of lumber surface as simultaneously scanned by the laser scanning device to perform a corresponding second scan;

FIG. 5a is a representation of the profile data obtained for the second pair of transverse areas associated with the second scan as shown in FIG. 5;

FIG. 5b is a representation of the profile data referred to in FIG. 5a, showing the partial twist indication resulting from a comparison with one another of the profile data characterizing the transverse areas in the scanning position shown in FIG. 5;

FIG. 6 is a schematic view of the piece of lumber at a scanning position N, showing a pair N of transverse areas of the piece of lumber surface as simultaneously scanned by the laser scanning device to perform a corresponding scan N;

FIG. 6a is a representation of the profile data obtained for pair N of transverse areas associated with scan N of FIG. 6;

FIG. 6b is a representation of the profile data referred to in FIG. 6a, showing the partial twist indication resulting from a comparison with one another of the profile data characterizing the transverse areas at the scanning position shown in FIG. 6;

FIG. 6c a representation of a variant form of profile data obtained for pair N of transverse areas associated with scan N of FIG. 6; and FIG. 6d is a representation of the profile data referred to in FIG. 6c, showing the partial twist indication resulting from a comparison with one another of the profile data characterizing the transverse areas at the scanning position shown in FIG. 6;

DETAILED DESCRIPTION OF THE PREFERRED EMBODIMENTS

Figure 1:
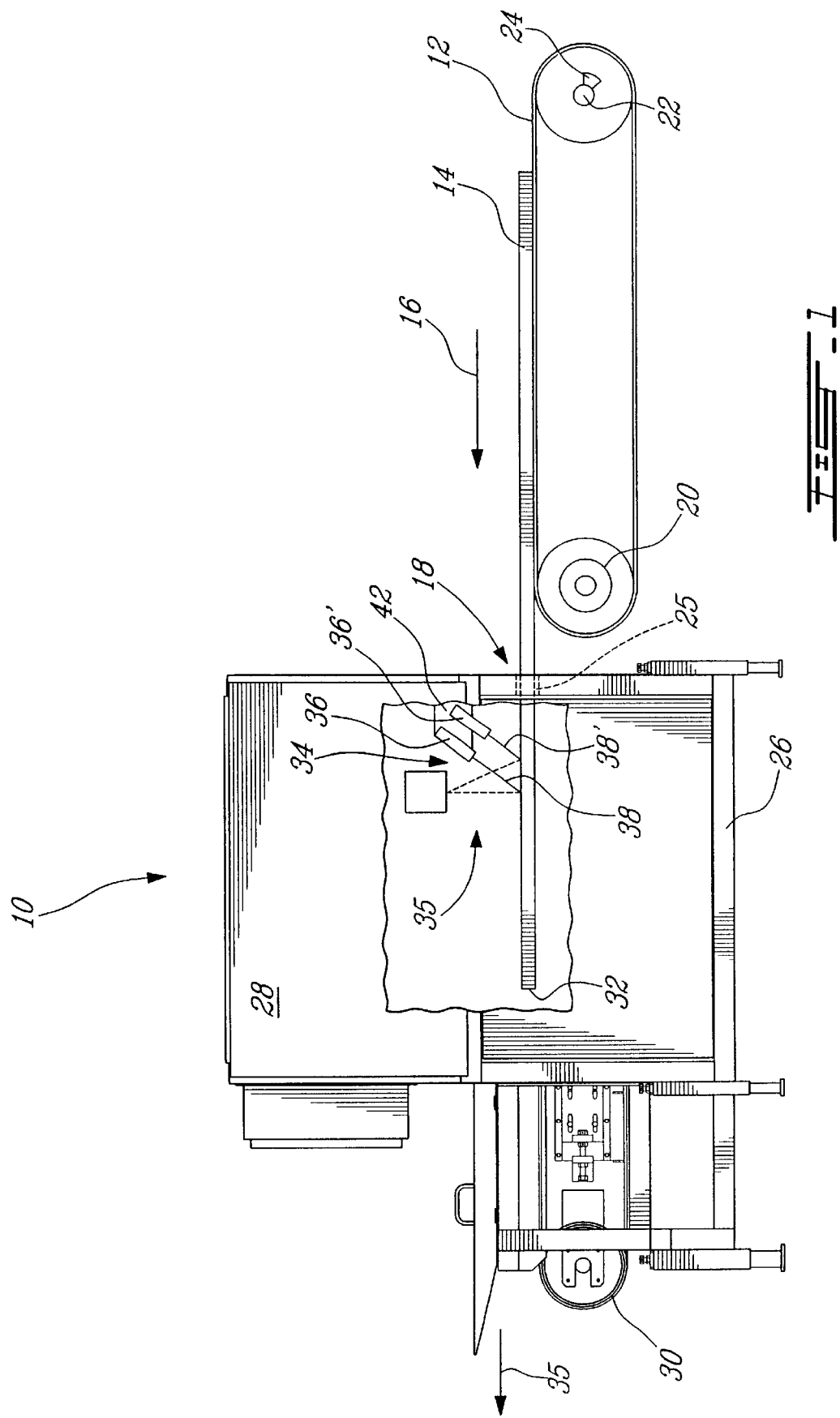
FIG. 1 is a side elevation view of a twist measuring apparatus according to a preferred embodiment of the invention, showing the two laser scanning devices.
Figure 2:
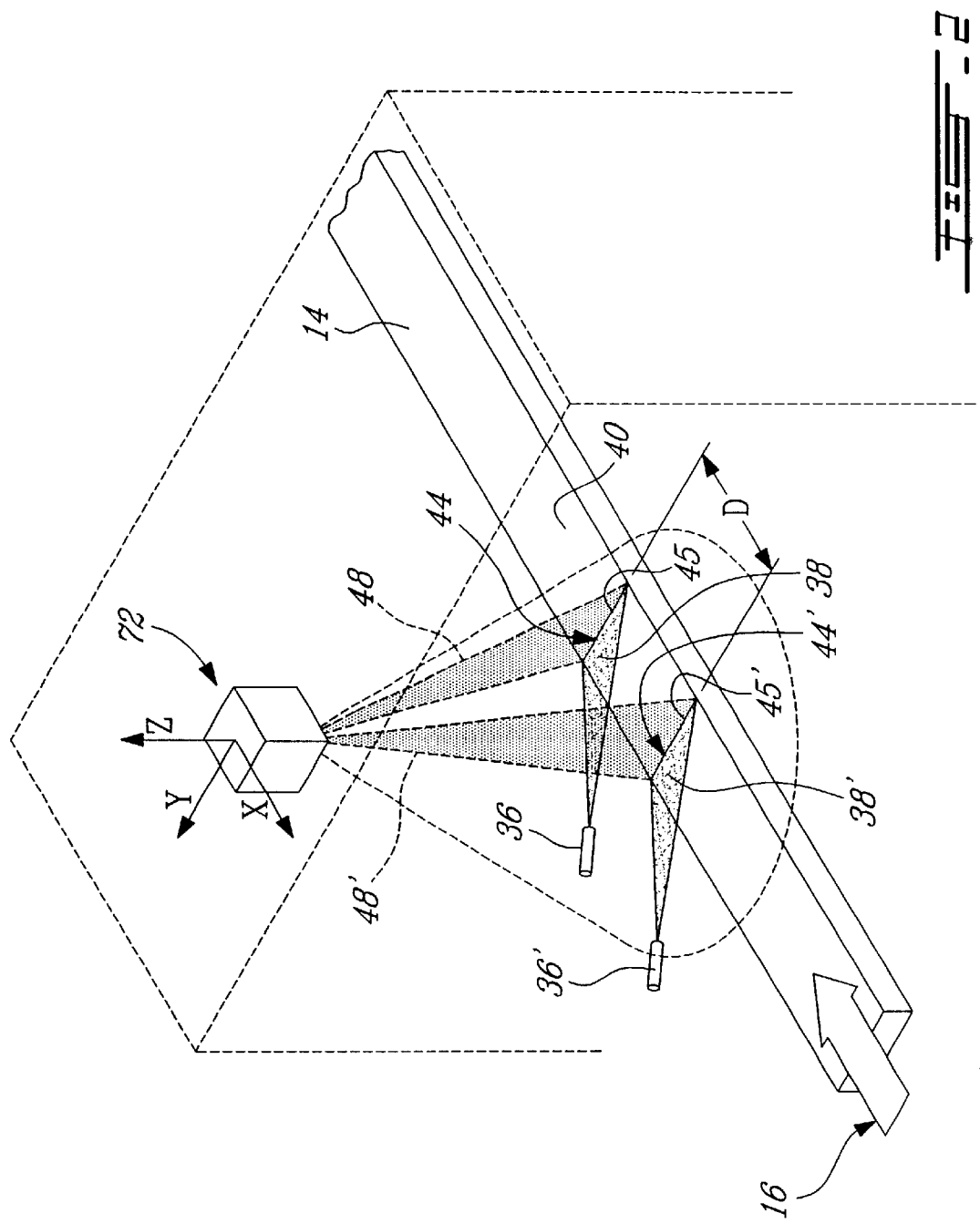
FIG. 2 is a schematic view of the optical sub-system of the laser scanning device provided on the apparatus of FIG. 1.

Referring now to FIG. 1, a twist measuring apparatus 10 according to a preferred embodiment of the invention is used in combination with transport means such as a belt conveyor 12 for feeding and elongated article 14, which is a piece of lumber for a main application of the present invention, in the direction of arrow 16 toward an input end 18 provided on the apparatus 10. The conveyor 12 includes a driving roll 20 being operatively coupled to a conventional electric motor (not shown) and an idle roll 22 which is coupled to a displacement sensing device including a position encoder 24 and a presence detector using photocells 25, the function of which will be explained later in detail. It is to be understood that any other type of electromechanical, electronic or optical displacement sensing device can also be used. The apparatus 10 has a main frame 26 supporting a main enclosure 28 a portion of which has been cut away in FIG. 1 to show a non-contact scanning device 34 provided on the apparatus 10, which is preferably a laser scanning device as part of a surface profile sensing unit generally designated at 35. At an output end of apparatus 10, transport means are also provided in the form of an output conveyor 30 capable of receiving a leading end 32 of piece of piece of lumber 14 for pulling thereof out of the apparatus 10 in the direction of arrow 35. The laser scanning device 34 includes a pair of laser sources 36, 36' for generating a pair of laser beams 38, 38' directed toward a same surface 40 of piece of lumber 14 as better shown in FIG. 2. The laser sources 36, 36' are adjustably secured to a holding member 42 attached to main frame 26 as shown in FIG. 1, in a spaced apart relationship in the conveying direction indicated by arrow 16, in such a manner that transverse scan line beams 38, 38' are directed toward the piece of lumber surface 40 in a corresponding spaced relationship in the conveying direction to form a pair of spaced transverse laser lines 44, 44' onto corresponding transverse areas 45, 45' of surface 40, distant one another by a predetermined spacing "D" as shown in FIG. 2. While laser sources 36, 36' are preferably disposed one relative to another so as to generate beams intersecting transverse areas laying in a parallel relationship, it is to be understood that any other appropriate laser sources configuration may be employed, provided reliable surface profile data can be obtained. The laser scanning device 34 also includes a digital camera 46 such a 640×480 pixels camera model no. UP-610 from Uniq Vision, Inc. (Santa Clara, Calif.) for capturing reflected light beams 48, 48' to generate electrical image signals from which profile data associated with scanned areas 45, 45' can be derived as will be explained below with reference to FIG. 3.

Figure 3:
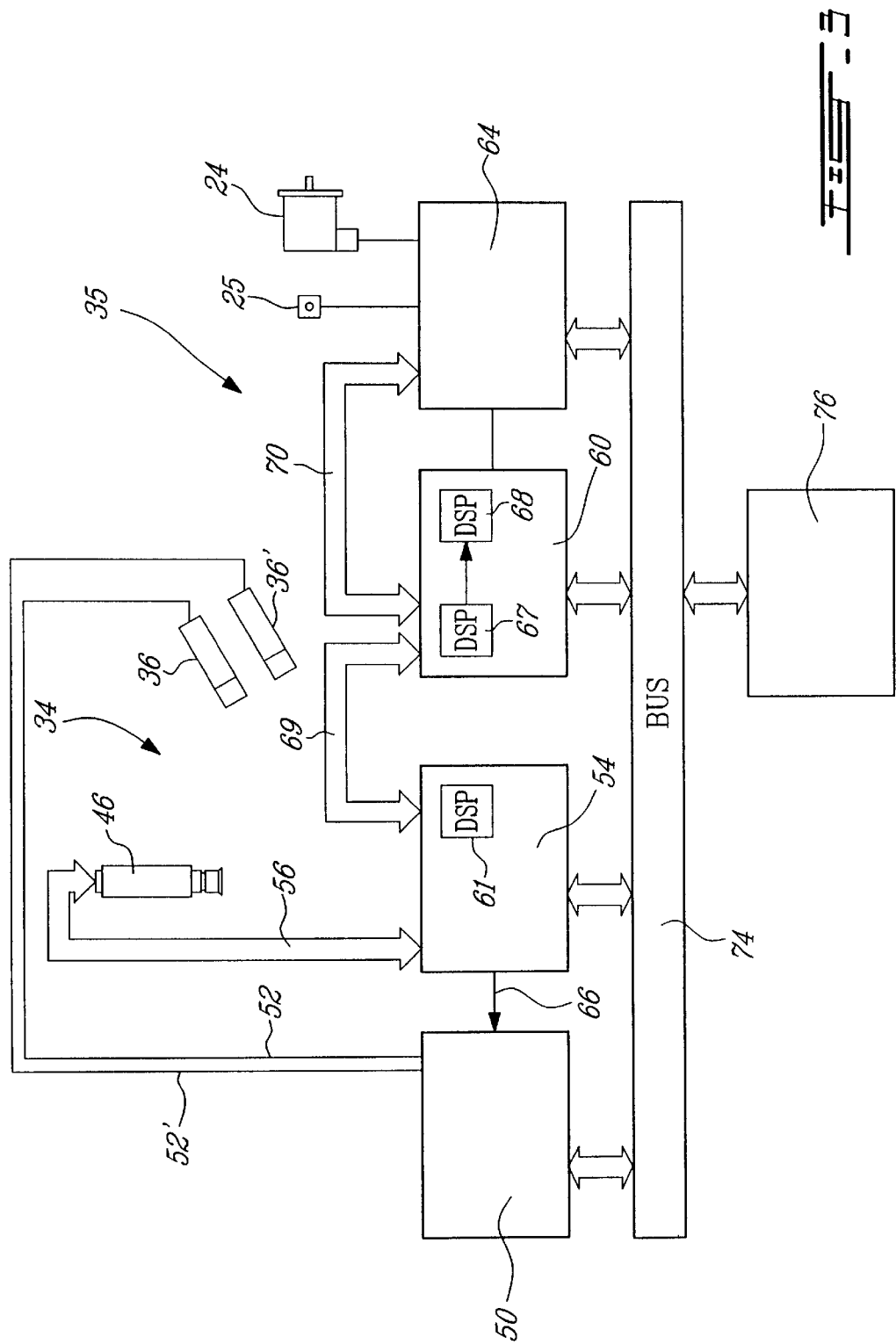
FIG. 3 is a schematic block diagram of the apparatus of FIG. 1.

As shown in FIG. 3, the laser scanning device 34 preferably includes a laser controller 50 for sending pulsed control signals to laser sources 36, 36' through links 52, 52', respectively, to provide synchronization of laser illumination with image capture, wherein illumination is limited to a fraction of the frame acquisition frequency of the camera, as well know by anyone skilled in the art. Alternatively, the laser controlling function may be performed directly by a camera controller/frame grabber in which case laser sources 36, 36' are energized in a continuous mode, provided the shutter speed of camera 46 is set high enough to avoid any adverse blurring effect due to high carrying speed of piece of lumber 14. To implement the laser controller 50, an off-the-shelf timer board can be used, such as a Computerboards model no. PCI DIO48/CTR15 based on 82C54 integrated circuit, or any equivalent board as supplied by Measuring Computing, Inc. (Middleboro, Mass.). The laser scanning device 34 further includes a camera controller/frame grabber board 54 that communicates with camera 46 through a bi-directional link 56 for sending a control signals thereto and receiving image signals therefrom. Implementation of camera controller/frame grabber 54 can be made with off-the-shelf image signal acquisition boards such as model no. Cobra/C6 from Coreco Imaging, Inc. (Montreal, Canada), which uses a TMS 320C6201 digital signal processor chip 61 from Texas Instruments. The camera controller/frame grabber is programmed to send, through an output link 66, a synchronization signal for triggering laser controller 50. The laser scanning device 34 including laser sources 36, 36', camera 46, laser controller 50 and camera controller/frame grabber 54 is part of the surface profile sensing unit 35, which further includes an image processing board 60 coupled to the displacement sensing device formed by position encoder 24 and presence detector 25, through an interface board 64. An Imola-PCI board from Spectrum Signal Processing, Inc. (Burnaby, Canada) or any other equivalent board may conveniently be used as encoder interface 64. The image processor board 60 can be a Daytona-PCI board making use of two digital signal processor chips 67,68 model TMS 320C6201 from Texas Instruments, or any other equivalent board. The first digital signal processor 67 can exchange data with laser controller/frame grabber 54 through a serial link 69 and with encoder interface 64 through a digital signal processor link 70. The second digital signal processor 68 of image processor board 60 is used to identify relevant portion of profile data generated by digital signal processor 67 and to store relevant data for all scanned areas 45, 45' of the surface 40 of piece of lumber 14. A further function of DSP 68 consists of identifying and storing opposed profile edge data that are sufficient to characterize the spatial position coordinates of a corresponding transverse area in a reference system 72, as will be later explained in more detail. The resulting processed profile data characterizing the position of each transverse area with respect to reference system 72, as illustrated on FIG. 2 in a location conveniently chosen to correspond to the camera location, are sent through a main PCI bus 74 to a data processor or host computer 76 capable of running analysis software according to a method that will be later explained in detail. The PCI bus 74 is also used by the computer 76 to exchange control data with the laser controller 50, camera controller/frame grabber 54, image processor board 60 and encoder interface 64. Any fast processing computer such as one provided with one or more Intel Pentium III microprocessors can be used to implement the data processing functions in accordance with the present invention.

Figure 4:
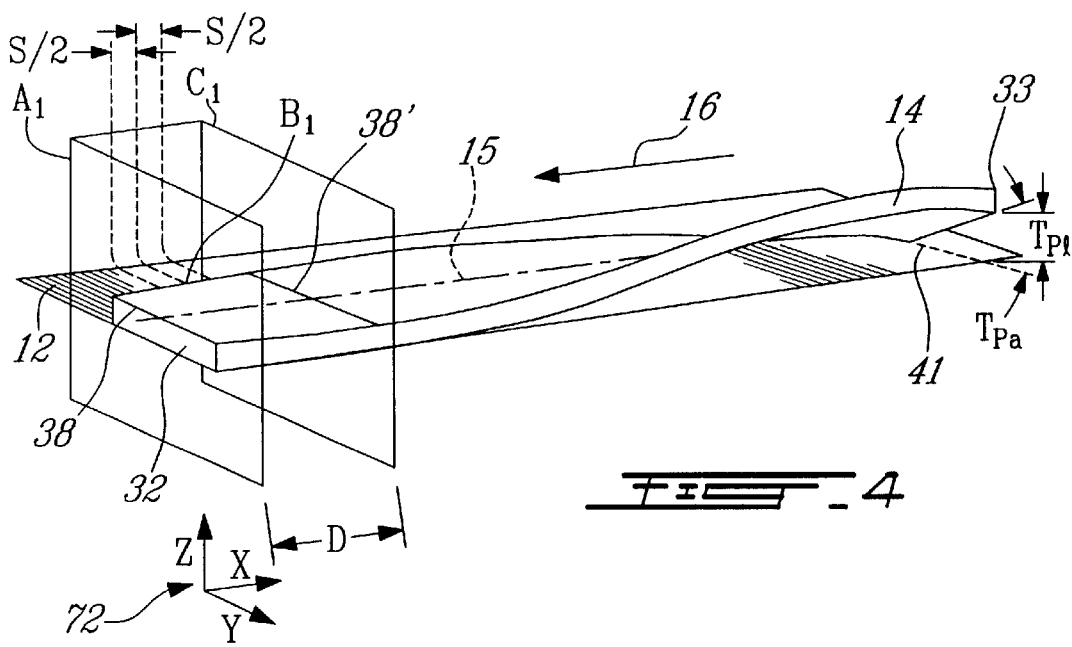
FIG. 4 is a schematic view of a piece of piece of lumber in a first scanning position showing a first pair of transverse areas of the piece of lumber surface as simultaneously scanned by the laser scanning device to perform a corresponding first scan.

A preferred mode of operation of the apparatus and method according to the present invention will be now explained in detail with reference to FIGS. 4–7b in view of FIGS. 2 and 3. Referring to FIG. 4, there is illustrated the piece of piece of lumber 14 defining a reference axis 15 usually extending lengthwise for typical lumber twist, with respect to which a twist indication value represented by $T_{Pl}$ or $T_{Pa}$ is illustrated in FIG. 4, as expressed in linear or angular form, respectively. A generally accepted procedure to measure twist in a piece of lumber consists of maintaining a first end of the piece of lumber 14, such as leading end 32 shown in FIG. 4, in contact against a planar surface, and then measuring at the opposed end of piece of lumber 14, such as trailing end 33 having its first corner 41 in contact with the planar surface as represented by the surface of conveyer 12, the maximum spacing between piece of lumber end 33 and the surface of conveyor 12, which spacing corresponds to the twist indication value for $T_{Pl}$ in its linear form. The piece of lumber 14 shown in FIG. 4 is moving in a conveying direction indicated by arrow 16 that is substantially parallel to reference axis 15, while the piece of lumber 14 is subjected to some wobbling movement relative to the conveying surface of conveyor 12. FIG. 4 illustrates the piece of lumber 14 just after its leading end 32 has passed through the sensing range of the presence detector 25 shown in FIG. 3, in a first scanning position wherein a first pair of transverse areas 38, 38' are simultaneously scanned by the laser scanning device 34 at a time $t_1$ associated with a first scan defined by a corresponding pair of transverse scanning planes $A_1$ and $C_1$, intersecting first pair of transverse areas 38, 38' at a corresponding article cross-section of the piece of lumber 14, so that the twist indication represents substantially an actual measurement of the twist in the considered portion of the piece of lumber 14. It can be seen from FIG. 4 that the scanning planes $A_1$ and $C_1$, are spaced apart according to a spacing "D" as explained before with reference to FIG. 2. The electrical image signal representing pixel values of a complete image frame including illuminated transverse areas 38, 38' is sent by camera 46 through link 56 to the camera controller/frame grabber 54 where the DSP 61 thereof selects and stores only pixels that correspond to illuminated areas 38, 38' thereby discarding other irrelevant pixels. Relevant pixel data is then sent to the first DSP 67 of image processor 60 that at first localize pixels corresponding to respective centers of illuminated areas 38, 38' followed by a sub-pixel interpolation to improve image resolution, as well known by anyone skilled in the art. Then, the DSP 67 performs triangulation processing on pixel data to generate profile data characterizing the position of each transverse area 38, 38' according to reference system 72 at initial time to preferably according to the profiling method disclosed in U.S. Pat. No. 6,122,065 issued to the present assignee on Sep. 19, 2000, which prior patent is incorporated herein by reference. It is to be understood that any other usual equivalent profile ranging technique can be used by DSP 67 to generate profile information. The DSP 67 has also the task of associating profile data corresponding to each transverse area 38, 38' with a corresponding longitudinal position on the piece of lumber 14 along axis X of reference system 72. For so doing, the DSP 67 receives from encoder 24 through interface 64 the position signal of encoder 24 which, when interpreted in relation with the signal of presence detector 24 produced as the leading end 32 of piece of lumber 14 enters the apparatus 10, represents a signal indicating the instantaneous position on scanned surface of the piece of lumber 14 with reference to the leading end 32 thereof, so as to provide an accurate indication of the relative longitudinal position of each transverse areas 38, 38' with respect to the leading end position.

Figures 4A, 4B:
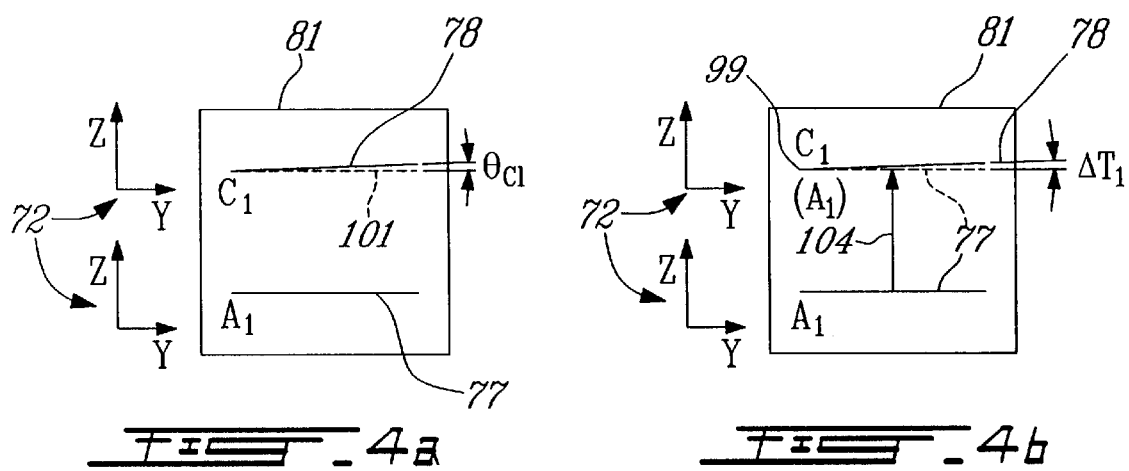
FIG. 4a is a representation of the profile data obtained for the first pair of transverse areas associated with the first scan as shown in FIG. 4.
FIG. 4b is a representation of the profile data referred to in FIG. 4a, showing the partial twist indication resulting from a comparison with one another of the profile data characterizing the transverse areas in the scanning position shown in FIG. 4.
Figure 8:
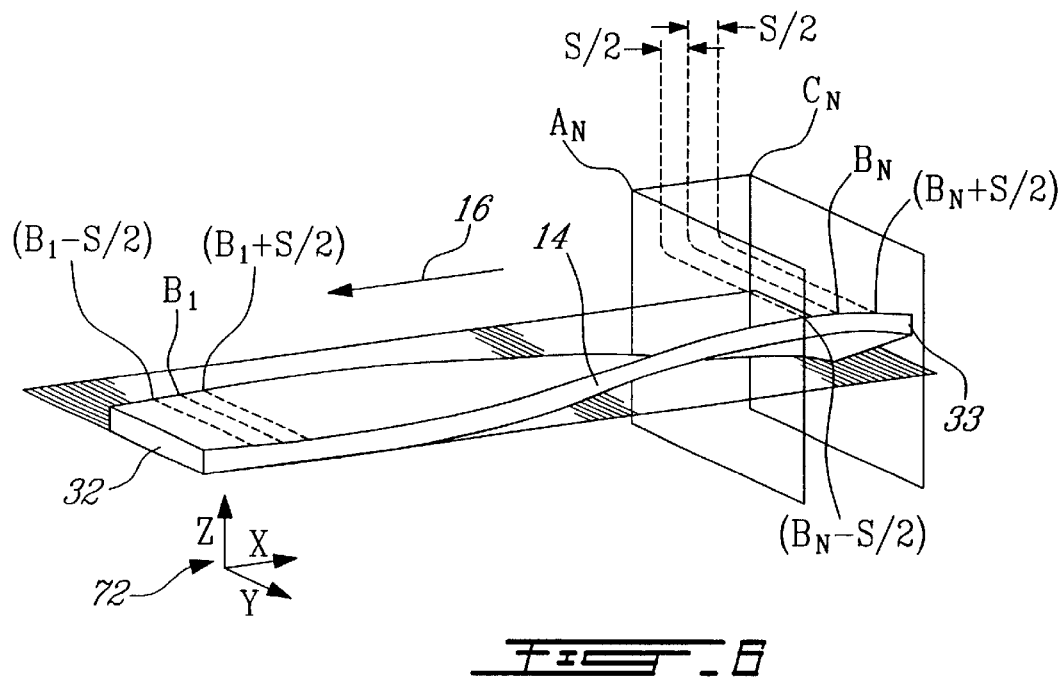
Figures 8A, 8B:
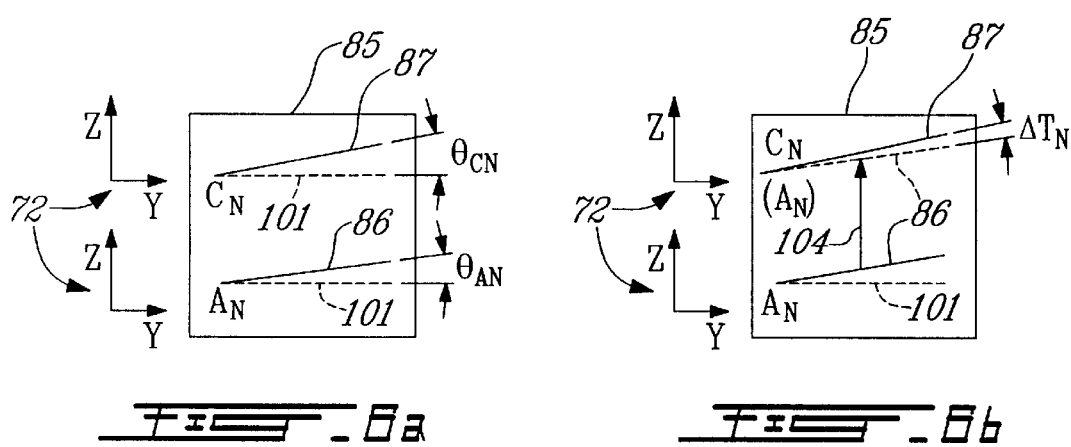
Figures 8C, 8D:
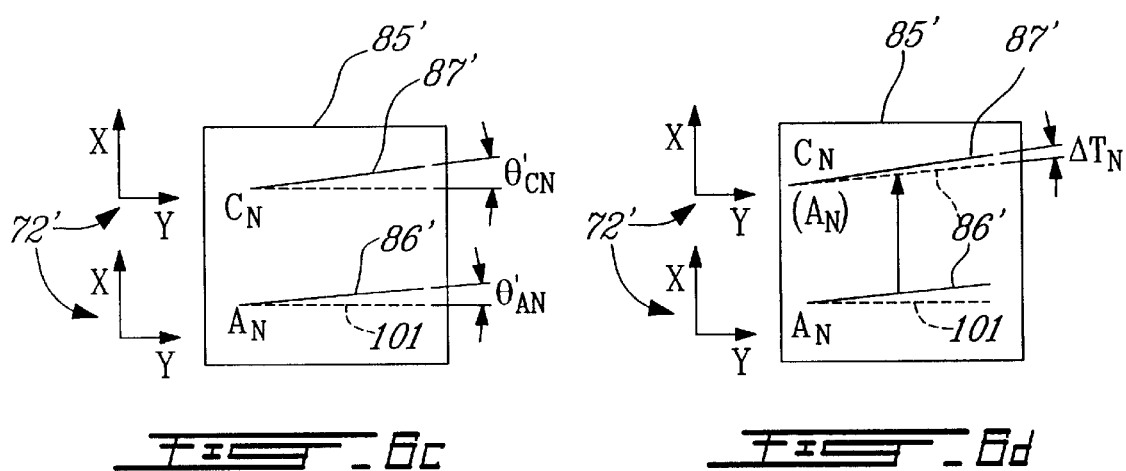

Turning now to FIG. 4a, profile data corresponding to transverse areas 38, 38' of FIG. 4 are shown respectively by profile line 77, 78, following a convenient superposition of scanning planes $A_1$ and $C_1$ relative to reference system 72 that has been duplicated for the purposes of illustration. The pair of profile lines 77, 78 represents the result of a first scan represented at 81 as performed by the surface profile sensing unit 35 of FIG. 3 at initial time $t_1$. The host computer 76 of FIG. 3 is programmed for comparing with one another the profile data characterizing transverse areas 38, 38' of first scan 81 to generate partial twist indicative data associated with said first scan. A preferred manner of performing that comparison step is illustrated in FIG. 4b, wherein profile line 77 has been translated as indicated by arrow 104 to a position adjacent profile line 78 wherein the spatial coordinates thereof share a common crossing point at 99 that has been conveniently chosen to correspond to respective left-side profile edges of profile lines 77 and 78, the latter being represented by truncated line following the translation. It can be appreciated in view of FIGS. 4a and 4b, that the angular variation between the profile data characterizing the transverse areas of the first scan 81 as represented by parameter $\Delta T_1$ can be obtained as follows:

$$\Delta T_1 = (\Theta_{C1} - \Theta_{A1})$$

wherein $\Theta_{A1}$ represents value of an angle formed by the spatial coordinates within scanning plane $A_1$ with respect to reference profile data represented by reference profile line 101, and $\Theta_{C1}$ represents value of and angle formed by the spatial coordinates within scanning plane $C_1$ with respect to the reference profile data. Conveniently, the reference profile data are given the same values as the data of profile line 77 associated with the first scan so that $\Theta_{A1}=0$, since twist measurement is generally made for a given portion of the piece of lumber 14 delimited by at least one of opposed ends 32, 33 thereof. Therefore, it is to be understood that the apparatus and method according to the present invention can be advantageously used for detecting twist of an article either over its whole length/width or over only a portion thereof. It is also to be understood that the computer 76 may be readily programmed to compare the profile data on the basis of a different crossing point located between opposed profiles edges of each profile line 77 or 78. To complete the comparison, applying appropriate apportionment to the angular variation parameter $\Delta T_1$, the computer 76 calculates the corresponding partial twist indication data as follows:

$$T_1 = \frac{\Delta T_1 \times S}{D} \tag{1}$$

Conveniently, the partial twist indication data $T_1$ for the first scan is associated with a position $B_1$ as shown in FIG. 4, representing an estimation of the partial twist over a distance S on a surface element of the article portion extending from $B_1-S/2$ to $B_1+S/2$, wherein $B_i$ is located at an intermediate distance $D/2$ from scanning planes $A_1$ and $C_1$ along the conveying direction 16 in the reference system 72 shown in FIG. 4.

Referring now to FIG. 5, the piece of lumber 14 is illustrated at a second scanning position wherein a second pair of transverse areas 39 and 39' of piece of lumber 14 are simultaneously scanned by the laser scanning device at a time $t_2>t_1$ to so that transverse area 39 intersected by corresponding scanning plane $A_2$ is spaced from transverse area 38 by a spacing S corresponding to the distance over which the partial twist is estimated. In other words, the scanning is repeatedly performed so as to substantially maintain an incremental spacing S between consecutive pairs of simultaneously scanned areas.

Turning now to FIG. 5a, profile data corresponding to transverse areas 39, 39' of FIG. 5 are shown respectively by profile line 79, 80, following a convenient superposition of scanning planes $A_2$ and $C_2$ relative to duplicated reference system 72. The pair of profile lines 79,80 represents the result of a second scan represented at 84 as performed at time $t_2$. In a same way as explained before, the host computer 76 of FIG. 3 compares with one another the profile data characterizing transverse areas 39, 39' of second scan 84 to generate partial twist indicative data associated with said second scan. Turning now to FIG. 5b in view of FIG. 5a, the angular variation $\Delta T_2$ between the profile data characterizing the transverse areas of the second scan 84 can be obtained as follows:

$$\Delta T_2 = (\Theta_{C2} - \Theta_{A2}) \tag{2}$$

wherein $\Theta_{A2}$ represents value of an angle formed by the spatial coordinates within scanning plane $A_2$ with respect to reference profile data represented by reference profile line 101, and $\Theta_{C2}$ represents value of and angle formed by the spatial coordinates within scanning plane $C_2$ with respect to the reference profile data. It can be seen from FIG. 5a that $\Theta_{A2}$ can have a value different from $\Theta_{A1}=0$, therefore indicating that a detected twist is associated with the position on the piece of lumber 14 intersected by scanning plane $A_2$. To complete the comparison, applying appropriate apportionment to the angular variation parameter $\Delta T_2$, the computer 76 calculates the corresponding partial twist indication data as follows:

$$T_2 = \frac{\Delta T_2 \times S}{D} \tag{3}$$

In a same manner as applied for the first scan, the partial twist indication data $T_2$ for the second scan is associated with a position $B_2$ as shown in FIG. 5, representing an estimation of the partial twist over a distance S on a area extending from $B_2-S/2$ to $B_2+S/2$. Having obtained partial twist indications $T_1$ and $T_2$ associated with first and second scans, respectively, the host computer 76 of FIG. 3 is further programmed for summing the partial twist indicative data associated with said scans to obtain an indication of the twist in the article portion defined between $B_1-S/2$ and $B_2+S/2$.

Referring now to FIG. 6, the piece of lumber 14 is illustrated at a final scanning position wherein a last pair of transverse areas (not shown) of piece of lumber 14 are simultaneously scanned by the laser scanning device at a time $t_N$ in a same way as explained before regarding the first and second scans in view of FIGS. 4 and 5.

Turning now to FIG. 6a, the profile data corresponding to the scanned transverse areas of last scan 85 are shown respectively by profile lines 86, 87, following superposition of scanning planes $A_N$ and $C_N$ relative to duplicated reference system 72. In a same way as explained before, the host computer 76 of FIG. 3 compares with one another the profile data characterizing the transverse areas of last scan 85 to generate partial twist indicative data associated with said last scan. Turning now to FIG. 6b in view of FIG. 6a, the angular variation $\Delta T_N$ between the profile data characterizing the second pair of transverse areas of the second scan 84 can be obtained as follows:

$$\Delta T_N = (\Theta_{CN} - \Theta_{AN}) \tag{4}$$

wherein $\Theta_{AN}$ represents value of an angle formed by the spatial coordinates within scanning plane $A_N$ with respect to reference profile data represented by reference profile line 101, and $\Theta_{CN}$ represents value of and angle formed by the spatial coordinates within scanning plane $C_N$ with respect to the reference profile data. It can be seen from the example shown in FIGS. 6a–6b in view of FIGS. 5a–5b that although $\Theta_{AN}$ and $\Theta_{CN}$ may have values significantly greater that $\Theta_{A2}$ and $\Theta_{C2}$, respectively, the calculated angular variation $\Delta T_N$ exhibits a value lower than $\Delta T_2$ in the example shown, reflecting the fact that the twist deforming the portion of piece of lumber 14 between scanning planes $A_2$ and $C_2$ is more important that the twist deforming the portion of the same piece of lumber between scanning planes $A_N$ and $C_N$. Although the relative wobbling movement between the piece of lumber 14 and the surface of conveyer 12 which may occurs during the inspection affects the spatial coordinates defined by scanning planes $A_N$, $C_N$ intersecting the transverse areas of the last scan, therefore affecting both the corresponding angle values $\Theta_{AN}$ and $\Theta_{CN}$, since these angles are measured simultaneously, the relative angle variation $\Delta T_N$ calculated therebetween is insensitive to the movement of piece of lumber 14 as it is transported on conveyer 12.

On the basis of the above calculations regarding first, second and last scans, a general expression for angular variation and partial twist indication for any considered scan can be proposed:

$$T_i = \frac{\Delta T_i \times S}{D} \quad (5)$$

$$\Delta T_i = (\Theta_{Ci} - \Theta_{Ai}) \quad (6)$$

wherein $T_i$ is partial twist indication data for a scan i, with i=1, ..., N, N being a number of scans preformed on the considered portion of piece of lumber 14, $\Delta T_i$ is a parameter representing angular variation between the profile data characterizing the pair of transverse areas of scan i, $\Theta_{Ai}$ represents value of the angle formed by the spatial coordinates within scanning plane $A_i$ with respect to the reference profile data, and $\Theta_{Ci}$ represents value of the angle formed by the spatial coordinates within scanning plane $C_i$ with respect to the reference profile data. According the generalization, to each scan i is associated a position $B_i$ conveniently located at an intermediate distance D/2 from scanning planes $A_i$ and $C_i$ along conveying direction 16 and reference system 72 shown in FIGS. 4, 5 and 6, each said partial twist indication data $T_i$ being associated with a corresponding surface element of said article portion extending from $B_i$–S/2 to $B_i$+S/2. It can be appreciated that the relative angle variation $\Delta Ti$ from any pair i of angles values $\Theta_{Ai}$ and $\Theta_{Ci}$ is insensitive to translation and/or rotation movement of piece of lumber 14 as it is transported on conveyer 12. Furthermore, the summation of partial twist indicative data as performed by the computer may be generally expressed in angular form as follows:

$$T_{Pa}\left(\sum_{i=1}^{N} T_i\right) \quad (7)$$

wherein $T_{Pa}$ is an angular value for the twist indication in the considered portion of piece of lumber 14. Since twist indication is usually expressed in term of a linear value, the computer may preferably calculate the linear twist indication as follows:

$$T_{Pl} = W \times \mathrm{Sin}\left(\sum_{i=1}^{N} T_i\right) \quad (8)$$

wherein W is the dimension of the article transverse to the reference axis and $T_{Pl}$ is a linear value for the twist indication in the considered portion of piece of lumber 14.

According to an alternate calculation approach aimed at reducing computing time, slope variation is estimated rather than angular variation in the following manner:

$$T_{Pa} = \mathrm{arcTan}\left(\sum_{i=1}^{N} T_i\right) \quad (9)$$

with $$\Delta T_i = \mathrm{Tan}(\Theta_{Ci} - \Theta_{Ai}); \quad (10)$$

considering that we have:

$$\mathrm{arcTan}\left(\sum_{i=1}^{N} T_i\right) \approx \sum_{i=1}^{N} \frac{(\Theta_{Ci} - \Theta_{Ai}) \times S}{D}$$

within a 1% error range for small angle variation values of about 10° and less. Similarly, when dealing with twist indication in its linear form we have:

$$T_{Pl} = W \times \mathrm{Sin}\left[\mathrm{arcTan}\left(\sum_{i=1}^{N} T_i\right)\right] \quad (11)$$

Turning back to FIG. 6, it can be seen that any twist associated with a surface element extending from leading end 32 to position $B_1$–S/2, just ahead the surface element delimited by $B_1$–S/2 and $B_1$+S/2, has not been considered by the calculation made hereinabove. Similarly, any twist associated with a surface element extending from trailing end 33 to position $B_N$+S/2, beyond surface element delimited by $B_N$–S/2 and $B_N$+S/2, has not been considered by the above calculation. Whereas twist estimation for a portion of the article excluding these end adjacent areas would be reliable in many applications, it may be desirable in some cases to obtain twist estimation for the whole article, in considering the twist contribution associated with these end adjacent areas. In such cases, which includes applications in lumber/timber industry, the article portion may be considered to extend from a leading end surface element and a trailing end surface element provided on the piece of lumber 14, and the summation of partial twist indicative data as performed by the computer may be generally expressed in angular form as follows:

$$T_{Pa} = \left(\sum_{i=1}^{N} T_i\right) + T_l + T_t \quad (12)$$

wherein $T_{Pa}$ is the angular value for twist indication in the article portion, $T_l$ is an estimated partial twist indication data associated with the leading end surface element and $T_t$ is an estimated partial twist indication data associated with the trailing end surface element. According to the usual linear form, the computer may preferably calculate the linear value for twist indication as follows:

$$T_{Pl} = W \times \mathrm{Sin}\left[\left(\sum_{i=1}^{N} T_i\right) + T_l + T_t\right] \quad (13)$$

According to the alternate calculation approach aimed at reducing computing time, wherein slope variation is estimated rather than angular variation, we have:

$$T_{Pa} = \mathrm{arcTan}\left[\left(\sum_{i=1}^{N} T_i\right) + T_l + T_t\right] \quad (14)$$

$$T_{Pl} = W \times \mathrm{Sin}\left[\mathrm{arcTan}\left[\left(\sum_{i=1}^{N} T_i\right) + T_l + T_t\right]\right] \quad (15)$$

for respectively calculating angular and linear values for twist indication.

In the embodiments described hereinabove, the profile data generated by the surface profile sensing unit via triangulation represent spatial coordinates, so that the twist indication obtained represents substantially an actual measurement of the twist in the considered portion of the scanned article. However, according to a variant approach, the profile data may be generated without any intermediary triangulation calculation, which profile data may be processed in a similar way as explained before, using a reference system 72' as duplicated in FIGS. 6c and 6d for the purposes of explanation. In FIG. 6c, the profile data corresponding to the scanned transverse areas of last scan N are shown respectively by profile lines 86', 87', following superposition of scanning planes $A_N$ and $C_N$ relative to duplicated reference system 72'. It can be seen from FIG. 6c in view of FIG. 6a that profile lines 86' and 87' of scan 85' define, with respect to reference line 101, corresponding angles $\Theta'_{AN}$ and $\Theta'_{CN}$ the values of which respectively differ from angle variations $\Theta_{AN}$ and $\Theta_{CN}$ shown in FIG. 6a, since the profile data shown in FIG. 6c have not been converted to actual spatial coordinates via triangulation, being expressed within an X-Y plane of reference system 72' extending substantially parallel to the length of piece of lumber 14 as opposed to plane Z-Y of reference system 72 shown in FIG. 6b. Consequently, the angular variation parameter $\Delta T_N$ of scan N shown in FIG. 6d obtained by comparing angle values of $\Theta'_{AN}$ and $\Theta'_{CN}$ according to equation (4) above, has a resulting value differing from $\Delta T_N$ shown in FIG. 6b, a finding that can be generalized to angle values $\Theta'_{Ai}$ and $\Theta'_{Ci}$ for any scan i according to equation (6) above. Accordingly, corresponding partial twist indication data $T_i'$ for each scan i as obtained according to the equation (5) above, as well as twist indication expressed either in angular and linear form, $T_{Pa}$ and $T_{Pl}$ as obtained through above equations (7), (9), (12), (14) and (8), (11), (13), (15), respectively differ from $T_i$, $T_{Pa}$ and $T_{Pl}$ as obtained with the same equations, since the latter parameters involve profile data corresponding to spatial coordinates. Although still representing some indication of a relative level of twist in the piece of lumber 14, it is to be understood that the resulting indication may be advantageously converted into an actual twist measurement through triangulation or any other equivalent technique. Moreover, it is to be understood that the profile data may either represent explicit coordinates of each relevant portion of the profile lines or be defined in term of algebraic relations from which such coordinates may be derived.

We claim:

1. An apparatus for detecting twist along a reference axis in at least a portion of an article being carried on a conveyer in a conveying direction substantially parallel to said reference axis, said apparatus comprising:

a surface profile sensing unit mounted with respect to said conveyor and provided with a non-contact scanning device directing a pair of transverse scan line beams onto a surface of said article in spaced relationship in the conveying direction and repeatedly performing scans of corresponding simultaneously scanned pairs of spaced transverse areas of said surface while the article is conveyed, to generate profile data characterizing position of each said transverse area in a reference system; and a data processor device for comparing with one another the profile data characterizing the respective position of the transverse areas of each said scan to generate partial twist indicative data associated with each said scan, and for summing the partial twist indicative data associated with all said scans to obtain an indication of the twist in said article portion.

2. The apparatus according to claim 1, wherein said non-contact scanning device is arranged so that said scan line beams are separated by a distance D, said scans being repeatedly performed so as to substantially maintain an incremental spacing S between consecutive said pairs of scanned areas.

3. The apparatus according to claim 1, further comprising a displacement sensing device capable of generating a signal indicating a scanning position on the surface of said article portion along the conveying direction and in said reference system, said data processor device being responsive to said scanning position signal to generate said partial twist indicative data.

4. The apparatus according to claim 3, wherein said non-contact scanning device is arranged so that said scan line beams are separated by a distance D, said scans being repeatedly performed so as to substantially maintain an incremental spacing S between consecutive said pairs of scanned areas.

5. The apparatus according to claim 1, wherein said profile data represent coordinates within a scanning plane intersecting each said transverse area through a corresponding cross-section of said article, so that said twist indication represents an actual measurement of the twist in said article portion.

6. A method for detecting twist along a reference axis in at least a portion of an article being carried on a conveyer in a conveying direction substantially parallel to said reference axis, said method comprising the steps of:

i) directing a pair of transverse scan line beams onto a surface of said article in spaced relationship in the conveying direction while repeatedly performing scans of corresponding simultaneously scanned pairs of spaced transverse areas of said surface while the article is conveyed, to generate profile data characterizing position of each said transverse area in a reference system;

ii) comparing with one another the profile data characterizing the respective position of the transverse areas of each said scan to generate partial twist indicative data associated with each said scan; and iii) summing the partial twist indicative data associated with all said scans to obtain an indication of the twist in said article portion.

7. The method according to claim 6, further comprising before said step ii) the step of:

a) sensing displacement of said article in the conveying direction to generate a signal indicating a scanning position on the surface of said article portion along said conveying direction and in said reference system;

wherein said comparing step ii) is performed using said scanning position signal to generate said partial twist indicative data.

8. The method according to claim 6, wherein said step i) is performed so that said scan line beams are separated by a distance D, said scans being repeatedly performed so as to substantially maintain an incremental spacing S between consecutive said pairs of scanned areas.

9. The method according to claim 8, wherein said comparing step ii) is defined by:

$$T_i = \frac{\Delta T_i \times S}{D}$$

wherein:

$T_i$ is said partial twist indication data for one said scan i, with i=1, . . . , N, N being a number of said scans preformed on said article portion;

$\Delta T_i$ is a parameter representing angular variation between said profile data characterizing said pair of transverse areas of one said scan i.

10. The method according to claim 9, wherein said summing step iii) is defined by:

$$T_{Pa} = \left(\sum_{i=1}^{N} T_i\right)$$

wherein:
$T_{Pa}$ is an angular value for said twist indication in said article portion.

11. The method according to claim 10, wherein said profile data represent spatial coordinates defined by N pairs of scanning planes $A_i$, $C_i$ intersecting N said pairs of transverse areas at corresponding cross-sections of said article so that said twist indication represents substantially an actual measurement of the twist in said article portion.

12. The method according to claim 11, wherein said angular variation parameter is expressed by:

$$\Delta T_i = (\Theta_{Ci} - \Theta_{Ai})$$

wherein:
$\Theta_{Ai}$ represents value of an angle formed by said spatial coordinates within said scanning plane $A_i$ with respect to reference profile data; and
$\Theta_{Ci}$ represents value of and angle formed by said spatial coordinates within said scanning plane $C_i$ with respect to reference profile data.

13. The method according to claim 12, wherein to each said scan i is associated a position $B_i$ located at an intermediate distance D/2 from said scanning planes $A_i$ and $C_i$ along said conveying direction in said reference system, each said partial twist indication data $T_i$ being associated with a corresponding surface element of said article portion extending from $B_i-S/2$ to $B_i+S/2$.

14. The method according to claim 9, wherein said summing step iii) is defined by:

$$T_{Pl} = W \times \mathrm{Sin}\left(\sum_{i=1}^{N} T_i\right)$$

wherein:
W is the dimension of said article transverse to said reference axis; and
$T_{Pl}$ is a linear value for said twist indication in said article portion.

15. The method according to claim 14, wherein said profile data represent spatial coordinates defined by N pairs of scanning planes $A_i$, $C_i$ intersecting N said pairs of transverse areas at corresponding cross-sections of said article so that said twist indication represents substantially an actual measurement of the twist in said article portion.

16. The method according to claim 15, wherein said angular variation parameter is expressed by:

$$\Delta T_i = (\Theta_{Ci} - \Theta_{Ai})$$

wherein:
$\Theta_{Ai}$ represents value of an angle formed by said spatial coordinates within said scanning plane $A_i$ with respect to reference profile data; and
$\Theta_{Ci}$ represents value of and angle formed by said spatial coordinates within said scanning plane $C_i$ with respect to reference profile data.

17. The method according to claim 16, wherein to each said scan i is associated a position $B_i$ located at an intermediate distance D/2 from said scanning planes $A_i$ and $C_i$ along said conveying direction in said reference system, each said partial twist indication data $T_i$ being associated with a corresponding surface element of said article portion extending from $B_i-S/2$ to $B_i+S/2$.

18. The method according to claim 9, wherein said summing step iii) is defined by:

$$T_{Pa} = \mathrm{arcTan}\left(\sum_{i=1}^{N} T_i\right)$$

with $$\Delta T_i = \mathrm{Tan}(\Theta_{Ci} - \Theta_{Ai});$$

wherein:
$\Theta_{Ai}$ represents value of an angle formed by said spatial coordinates within said scanning plane $A_i$ with respect to reference profile data;
$\Theta_{Ci}$ represents value of an angle formed by said spatial coordinates within said scanning plane $C_i$ with respect to the reference profile data; and
$T_{Pa}$ is an angular value for said twist indication in said article portion.

19. The method according to claim 18, wherein said profile data represent spatial coordinates defined by N pairs of scanning planes $A_i$, $C_i$ intersecting N said pairs of transverse areas at corresponding cross-sections of said article so that said twist indication represents substantially an actual measurement of the twist in said article portion.

20. The method according to claim 9, wherein said summing step iii) is defined by:

$$T_{Pl} = W \times \mathrm{Sin}\left[\mathrm{arcTan}\left(\sum_{i=1}^{N} T_i\right)\right]$$

with $$\Delta T_i = \mathrm{Tan}(\Theta_{Ci} - \Theta_{Ai});$$

wherein:
$\Theta_{Ai}$ represents value of an angle formed by said spatial coordinates within said scanning plane $A_i$ with respect to reference profile data;
$\Theta_{Ci}$ represents value of an angle formed by said spatial coordinates within said scanning plane $C_i$ with respect to the reference profile data;
W is the dimension of said article transverse to said reference axis; and
$T_{Pl}$ is a linear value for said twist indication in said article portion.

21. The method according to claim 20, wherein said profile data represent spatial coordinates defined by N pairs of scanning planes $A_i$, $C_i$ intersecting N said pairs of transverse areas at corresponding cross-sections of said article so that said twist indication represents substantially an actual measurement of the twist in said article portion.

22. The method according to claim 9, wherein said article portion extends from a leading end surface element and a trailing end surface element provided on said article, said summing step iii) being defined by:

$$T_{Pa} = \left(\sum_{i=1}^{N} T_i\right) + T_l + T_t$$

wherein:
- $T_{Pa}$ is an angular value for said twist indication in said article portion;
- $T_l$ is an estimated partial twist indication data associated with said leading end surface element; and
- $T_t$ is an estimated partial twist indication data associated with said trailing end surface element.

23. The method according to claim 22, wherein said profile data represent spatial coordinates defined by N pairs of scanning planes $A_i$, $C_i$ intersecting N said pairs of transverse areas at corresponding cross-sections of said article so that said twist indication represents substantially an actual measurement of the twist in said article.

24. The method according to claim 23, wherein said angular variation parameter is expressed by:

$$\Delta T_i = (\Theta_{Ci} - \Theta_{Ai})$$

wherein:
- $\Theta_{Ai}$ represents value of an angle formed by said spatial coordinates within said scanning plane $A_i$ with respect to reference profile data; and
- $\Theta_{Ci}$ represents value of an angle formed by said spatial coordinates within said scanning plane $C_i$ with respect to the reference profile data.

25. The method according to claim 24, wherein to each said scan i is associated a position $B_i$ located at an intermediate distance D/2 from said scanning planes $A_i$ and $C_i$ along said conveying direction in said reference system, each said partial twist indication data $T_i$ being associated with a corresponding surface element of said article portion extending from $B_i - S/2$ to $B_i + S/2$.

26. The method according to claim 25, wherein said estimated partial twist data are respectively expressed by:

$$T_i = \frac{\Delta T_i (D - S)}{2D}$$

and $$T_t = \frac{\Delta T_N (D - S)}{2D}.$$

27. The method according to claim 9, wherein said article portion extends from a leading end surface element and a trailing end surface element provided on said article, said summing step iii) being defined by:

$$T_{Pl} = W \times \mathrm{Sin}\left[\left(\sum_{i=1}^{N} T_i\right) + T_l + T_t\right]$$

wherein:
- W is the dimension of said article transverse to said reference axis;
- $T_{Pl}$ is a linear value for said twist indication in said article portion;
- $T_l$ is an estimated partial twist indication data associated with said leading end surface element; and
- $T_t$ is an estimated partial twist indication data associated with said trailing end surface element.

28. The method according to claim 27, wherein said profile data represent spatial coordinates defined by N pairs of scanning planes $A_i$, $C_i$ intersecting N said pairs of transverse areas at corresponding cross-sections of said article so that said twist indication represents substantially an actual measurement of the twist in said article.

29. The method according to claim 28, wherein said angular variation parameter is expressed by:

$$\Delta T_i = (\Theta_{Ci} - \Theta_{Ai})$$

wherein:
- $\Theta_{Ai}$ represents value of an angle formed by said spatial coordinates within said scanning plane $A_i$ with respect to reference profile data; and
- $\Theta_{Ci}$ represents value of an angle formed by said spatial coordinates within said scanning plane $C_i$ with respect to the reference profile data.

30. The method according to claim 29, wherein to each said scan i is associated a position $B_i$ located at an intermediate distance D/2 from said scanning planes $A_i$ and $C_i$ along said conveying direction in said reference system, each said partial twist indication data $T_i$ being associated with a corresponding surface element of said article portion extending from $B_i - S/2$ to $B_i + S/2$.

31. The method according to claim 30, wherein said estimated partial twist data are respectively expressed by:

$$T_i = \frac{\Delta T_1 (D - S)}{2D}$$

and $$T_t = \frac{\Delta T_N (D - S)}{2D}.$$

32. The method according to claim 9, wherein said summing step iii) is defined by:

$$T_{Pa} = \mathrm{arcTan}\left[\left(\sum_{i=1}^{N} T_i\right) + T_l + T_t\right]$$

with $$\Delta T_i = \mathrm{Tan}(\Theta_{Ci} - \Theta_{Ai})$$

wherein:
- $\Theta_{Ai}$ represents value of an angle formed by said spatial coordinates within said scanning plane $A_i$ with respect to reference profile data;
- $\Theta_{Ci}$ represents value of and angle formed by said spatial coordinates within said scanning plane $C_i$ with respect to reference profile data; and
- $T_{Pa}$ is an angular value for said twist indication in said article portion.

33. The method according to claim 9, wherein said summing step iii) is defined by:

$$T_{Pl} = W \times \operatorname{Sin}\left[\operatorname{arcTan}\left[\left(\sum_{i=l}^{N} T_i\right) + T_l + T_t\right]\right]$$

with $$\Delta T_i = \operatorname{Tan}(\Theta_{Ci} - \Theta_{Ai});$$

wherein:

$\Theta_{Ai}$ represents value of an angle formed by said spatial coordinates within said scanning plane $A_i$ with respect to reference profile data;

$\Theta_{Ci}$ represents value of an angle formed by said spatial coordinates within said scanning plane $C_i$ with respect to the reference profile data;

W is the dimension of said article transverse to said reference axis; and $T_{Pl}$ is a linear value for said twist indication in said article portion.

* * * * *

UNITED STATES PATENT AND TRADEMARK OFFICE
CERTIFICATE OF CORRECTION

PATENT NO. : 6,708,122 B2
DATED : March 16, 2004
INVENTOR(S) : Lessard et al.

It is certified that error appears in the above-identified patent and that said Letters Patent is hereby corrected as shown below:

Column 3,
Line 24, "the piece of piece" should read -- the piece --.

Column 4,
Line 14, "the piece of piece" should read -- the piece --.

Column 6,
Line 23, "to" should read -- $t_1$ --.

Column 7,
Line 28, "$B_i$" should read -- $B_1$ --.
Line 46, "line" should read -- lines --.

Column 9,
Line 9, "preformed" should read -- performed --.

Column 12,
Line 64, "preformed" should read -- performed --.

Column 13,
Lines 26 and 63, "and" should read -- an --.

Signed and Sealed this

Third Day of August, 2004

JON W. DUDAS
*Acting Director of the United States Patent and Trademark Office*